(12) United States Patent
Basawaraj Patil Okaly et al.

(10) Patent No.: US 11,419,559 B2
(45) Date of Patent: Aug. 23, 2022

(54) DEVICE, SYSTEM, AND METHOD FOR DETECTING AND DETERMINING CARDIAC AND NON-CARDIAC PAIN

(71) Applicant: KONINKLIJKE PHILIPS N.V., Eindhoven (NL)

(72) Inventors: Vikram Basawaraj Patil Okaly, Eindhoven (NL); Ravindra Balasaheb Patil, Eindhoven (NL); Rithesh Sreenivasan, Eindhoven (NL); Krishnamoorthy Palanisamy, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 24 days.

(21) Appl. No.: 16/770,331

(22) PCT Filed: Dec. 3, 2018

(86) PCT No.: PCT/EP2018/083271
§ 371 (c)(1),
(2) Date: Jun. 5, 2020

(87) PCT Pub. No.: WO2019/110467
PCT Pub. Date: Jun. 13, 2019

(65) Prior Publication Data
US 2020/0352519 A1    Nov. 12, 2020

Related U.S. Application Data

(60) Provisional application No. 62/635,594, filed on Feb. 27, 2018.

(30) Foreign Application Priority Data

Dec. 8, 2017 (IN) .............................. 201741044098

(51) Int. Cl.
*A61B 5/00* (2006.01)
*G16H 50/30* (2018.01)
(Continued)

(52) U.S. Cl.
CPC .......... *A61B 5/7264* (2013.01); *A61B 5/0006* (2013.01); *A61B 5/0205* (2013.01);
(Continued)

(58) Field of Classification Search
CPC ... A61B 5/7264; A61B 5/0006; A61B 5/0205; A61B 5/4824; A61B 5/4884;
(Continued)

(56) References Cited

U.S. PATENT DOCUMENTS 6,171,256 B1 * 1/2001 Joo .......................... A61B 5/30
600/508
8,626,275 B1    1/2014 Amit et al.
(Continued)

FOREIGN PATENT DOCUMENTS

WO    1999055226 A1    11/1999
WO    2017012906 A1    1/2017

OTHER PUBLICATIONS

"Hong Yan and Yanjun Li, Electrocardiogram Analysis based on the Karhunen-Loeve Transform", 2010 3rd International Conference on Biomedical Engineering and Informatics (BMEI 2010), 2010, pp. 887-890 (Year: 2010).*

(Continued)

*Primary Examiner* — Joseph M Dietrich
*Assistant Examiner* — Michael T. Holtzclaw (57) ABSTRACT

A device, system, and method is provided for detecting pain in a cardiac-related region of the body and determining whether that pain is cardiac or non-cardiac. The device, system, and method may include calculating or determining a first feature based on a variation in activity level and a (Continued)

variation in the detected heartrate measurement and a second feature based on a variation in the detected ECG features and a first feature and then subjecting at least the first feature and the second feature to a cardiac pain classifier to determine a cardiac classification.

18 Claims, 4 Drawing Sheets

(51) Int. Cl.
  *A61B 5/024*    (2006.01)
  *A61B 5/11*    (2006.01)
  *A61B 5/349*    (2021.01)
  *G16H 40/67*    (2018.01)
  *A61B 5/0205*    (2006.01)
  *A61B 5/01*    (2006.01)
  *A61B 5/08*    (2006.01)

(52) U.S. Cl.
  CPC .......... *A61B 5/4824* (2013.01); *A61B 5/4884* (2013.01); *A61B 5/7253* (2013.01); *A61B 5/7285* (2013.01); *G16H 40/67* (2018.01); *G16H 50/30* (2018.01); *A61B 5/01* (2013.01); *A61B 5/02405* (2013.01); *A61B 5/02438* (2013.01); *A61B 5/08* (2013.01); *A61B 5/1118* (2013.01); *A61B 5/349* (2021.01); *A61B 2562/029* (2013.01); *A61B 2562/0219* (2013.01)

(58) Field of Classification Search
  CPC ..... A61B 5/7253; A61B 5/7285; A61B 5/349; A61B 5/02405; A61B 5/02438; A61B 5/1118; G16H 40/67; G16H 50/30
  See application file for complete search history.

(56) References Cited

U.S. PATENT DOCUMENTS

| | | | |
|---|---|---|---|
| 2005/0004485 A1* | 1/2005 | Crosby | G01N 33/6893 600/513 |
| 2007/0066904 A1* | 3/2007 | Wiesmann | A61B 5/05 600/508 |
| 2012/0179055 A1* | 7/2012 | Tamil | A61B 5/726 600/509 |
| 2013/0281816 A1 | 10/2013 | Strauss et al. | |
| 2014/0276122 A1* | 9/2014 | Dulak | A61B 5/4836 600/483 |
| 2016/0135706 A1* | 5/2016 | Sullivan | A61N 1/37211 600/301 |
| 2017/0100062 A1* | 4/2017 | Marmor | A61B 5/1102 |
| 2017/0300653 A1* | 10/2017 | Hresko | G16H 40/60 |
| 2021/0100469 A1* | 4/2021 | Al-Zaiti | A61B 5/363 |

OTHER PUBLICATIONS

"Bruno Stecanella, An Introduction to Support Vector Machines (SVM), Jun. 22, 2017, MonkeyLearn" (Year: 2017).*
International Search Report and Written Opinion, International Application No. PCT/EP2018/083271, dated Mar. 29, 2019.
Leijdekkers, P. et al., "A Self-test to Detect a Heart Attack Using a Mobile Phone and Wearable Sensors", 21st IEEE International Symposium on Computer-Based Medical Systems, 2008.

* cited by examiner

DEVICE, SYSTEM, AND METHOD FOR DETECTING AND DETERMINING CARDIAC AND NON-CARDIAC PAIN

This application is the U.S. National Phase application under 35 U.S.C. § 371 of International Application No. PCT/EP2018/083271, filed on 3 Dec. 2018, which claims the benefit of U.S. Provisional Application No. 62/635,594, filed 27 Feb. 2018 and Indian Application No. 201741044098, filed 8 Dec. 2017. These applications are hereby incorporated by reference herein.

FIELD OF THE DISCLOSURE

The present invention relates to a device, system, and method for detecting pain in a cardiac-related region of the body and determining whether that pain is cardiac or non-cardiac related.

BACKGROUND OF THE DISCLOSURE

The term "chest pain" is commonly associated with heart attacks or other types of cardiac conditions such as angina. In fact, roughly half of the chest pain cases seen by doctors are of cardiac origin. The remaining 50% is referred to as non-cardiac chest pain (NCCP), which may be a result of another disease causing pain in the chest. For example, cervical disc diseases, such as cervical spondylosis without neuropathy and cervical strain; gastric conditions, such as gastritis, oesphagitis, and gastroesophageal reflux disease (GERD); costochonritis; and/or other local musculoskeletal diseases may present chest pain. People with these diseases may underestimate chest pain and choose not to seek medical attention when necessary. Thus, it is imperative for people to be able to differentiate between cardiac and non-cardiac pain in order to properly seek medical attention.

Current systems of differentiating between cardiac and non-cardiac pain may do so by using exercise, but require surrogate signals such as blood pressure, heartrate, temperature, or respiratory rate to determine whether a patient is exercising and then characterize an event as exercise-related or non-exercise related. Additionally, current systems cannot differentiate between cardiac and non-cardiac pain using a patient-specific protocol and are not available outside of a clinical setting. These and other drawbacks exist.

Various embodiments described herein seek to solve these drawbacks by providing a system, device, and method capable of classifying pain as cardiac or non-cardiac without surrogate signals to determine exercise data, wherein the systems, devices, and methods described herein provide a patient-specific protocol that may be used in any setting.

SUMMARY OF THE DISCLOSURE

Various embodiments of the present disclosure provide a device, system, and method for detecting and determining whether pain is cardiac or non-cardiac related. Various embodiments of the present disclosure provide a device, system, and/or method to accurately determine activity levels and electrocardiogram and heartrate features to differentiate the chest pain is of cardiac or non-cardiac nature.

Various embodiment may include an input/output interface that receives data indicative of chest pain and transmits a notification to begin electrocardiogram (ECG) measurements; and a processor that: generates a set of instructions for the user, wherein the set of instructions includes instructions with varying levels of difficulty; receives a set of measurements from a wearable device housing an ECG sensor comprising a heartrate measurement and at least one ECG feature, wherein the set of measurements are received as the user is following the generated set of instructions, and wherein the ECG features comprise at least one of: Karhunen-Loeve transform (KLT) components of an ST segment of the ECG measurement or a PQ segment of the ECG measurement, a time interval from R peak to P off-set and P peak, a time interval from R peak to S, and a time interval from S to J point; classifies the ischemic change as cardiac or non-cardiac by: (a) determining a first feature based on a variation in activity level and a variation in the detected heartrate measurement; (b) determining a second feature based on a variation in the detected ECG features and a first feature; (c) subjecting the first features and the second feature to a cardiac pain classifier to determine a cardiac classification; and transmitting the cardiac classification via the input/output interface.

Various embodiments described herein may include subjecting the ECG feature along with the first feature and the second feature to the cardiac pain classifier.

Various embodiments described herein may include using a set of instructions for the user are generated based on a detected initial ischemic change measured using the wearable device while the user is non-ambulatory.

Various embodiments described herein may include a set of measurements such as an activity level measurement including at least one of: a mean value of activity level measurements, a moving average of activity level measurements, an active time associated with activity level measurements, a moving average of variation in activity level measurements, and a moving average of an active time associated with activity level measurements.

Various embodiments described herein may include an activity level measurement including at least one of: a distance, a number of steps, and an elevation. Various embodiments described herein may include an activity level measurements including at least one of: a distance measurement, a step count measurement, and a speed measurement.

Various embodiments described herein may include using a support vector machine (SVM) classifier as a cardiac pain classifier.

Various embodiments described herein may include a heartrate measurement that includes at least one of: a variability of heartrate within a predefined interval and a moving average of variation in heartrate computed during a predefined interval.

Various embodiments described herein may include a first feature of $w_{11}$ when (a) there is no variation in activity level and no variation in heartrate measurement, (b) there is a decrease in activity level and no variation in heartrate measurement, (c) there is an increase in activity level and an increase in heartrate measurement, (d) there is an increase in activity level and a decrease in heartrate measurement, or (e) there is a decrease in activity level and a decrease in heartrate measurement; and/or a first feature of $w_{12}$ when there is a decrease in activity level and an increase in heartrate measurement, wherein $w_{11} < w_{12}$. Various embodiments described herein may include a second feature of $w_{22}$ when there is a variation in an ECG feature and the first feature is $w_{11}$, and/or a second feature of $w_{23}$ when there is a variation in an ECG feature and the first feature is $w_{12}$, wherein $w_{22} < w_{23}$.

Various embodiments described herein may include classifying the ischemic change continuously during a predefined amount of time that dynamically changes based on the classifying.

In various embodiments, a device, system, and/or method may include an augmented system with an input/output interface that receives data indicative of chest pain, generates a notification to begin electrocardiogram (ECG) measurements, and receives ECG measurements from a wearable device housing an ECG sensor.

In various embodiments, a device, system and/or method may include an augmented system with a processor that detects initial measurements, wherein the initial measurements comprise ECG measurements taken while a user associated with the wearable device is non-ambulatory for a first predefined amount of time, wherein the predefined amount of time may be after the input/output receives data indicative of chest pain; determines that the initial measurements are indicative of requiring additional data to determine whether the data indicative of chest pain is cardiac; generates a set of instructions for the user based on the detected initial ischemic change in ECG; detects second measurements comprising an activity level measurement and ECG features based on second ECG measurements, wherein the second measurements are taken while the wearer is ambulatory and following the generated set of instructions for a second predefined amount of time, and wherein the ECG features comprise at least one of: Karhunen-Loeve transform (KLT) components of an ST segment of the ECG measurement or a PQ segment of the ECG measurement, a time interval from R peak to P off-set and P peak, a time interval from R peak to S, and a time interval from S to J point; determines an ischemic change based on the second measurements; and classifies the ischemic change as cardiac or non-cardiac by calculating features using at least the activity level measurement and the ECG features and subjecting the features to a support vector machine (SVM) classifier, wherein the classified ischemic change is transmitted via the input/output interface to a third party device.

In various embodiments, a device, system, and/or method may include heartrate-based features including at least one of: a variability of heartrate with a predefined interval and a moving average of variation in heartrate computed and updated during a predefined interval.

In various embodiments, a device, system, and/or method may include using a one minute predefined interval for both the variability of heartrate and the moving average of variation in heartrate.

In various embodiments, a device, system, and/or method may include a first predefined amount of time associated with the initial measurements or ECG measurements taken while a user associated with the wearable device is non-ambulatory may be one, two, three, five, or ten minutes, or the like. In various embodiments, the second predefined amount of time associated with the generated set of instructions may be one, two, three, five, ten, fifteen, twenty, or thirty minutes, or the like.

In various embodiments, a device, system, and/or method may include a set of instructions, which may be a dynamic set of instructions including, but not limited to, instructions for moderate exercise (e.g., brisk walking, biking, swimming, or the like), instructions for increased difficulty of exercise (e.g., jogging, increasing a walking incline, increasing speed, incline, and/or resistance for biking, increasing speed and/or resistance for swimming, jumping rope, and/or the like), and instructions for cool down exercises (e.g., walking, stretching, breathing exercises, and/or the like).

In various embodiments, a device, system, and/or method may include classifying the ischemic change continuously during the second predefined amount of time. In various embodiments, a device, system and/or method may include a second predefined amount of time associated with a set of instructions changing dynamically based on a classification of an ischemic change.

Various embodiments may include a dynamic set of instructions comprising instructions for moderate exercise, instructions for increased difficulty of exercise, and instructions for cool down exercises.

BRIEF DESCRIPTION OF THE DRAWINGS

Various embodiments of the present disclosure, together with further objects and advantages, may best be understood by reference to the following description taken in conjunction with the accompanying drawings, in the several Figures of which like reference numerals identify like elements, and in which.

DETAILED DESCRIPTION OF THE EMBODIMENTS

The following description is intended to convey a thorough understanding of the embodiments described by providing a number of specific exemplary embodiments and details involving a device, system, and method for detecting pain in a cardiac-related region of the body and determining whether that pain is cardiac or non-cardiac related. It should be appreciated, however, that the present disclosure is not limited to these specific embodiments and details, which are examples only. It is further understood that one possessing ordinary skill in the art, in light of known systems and methods, would appreciate the use of the invention for its intended purposes and benefits in any number of alternative embodiments, depending on specific design and other needs.

Figure 1:
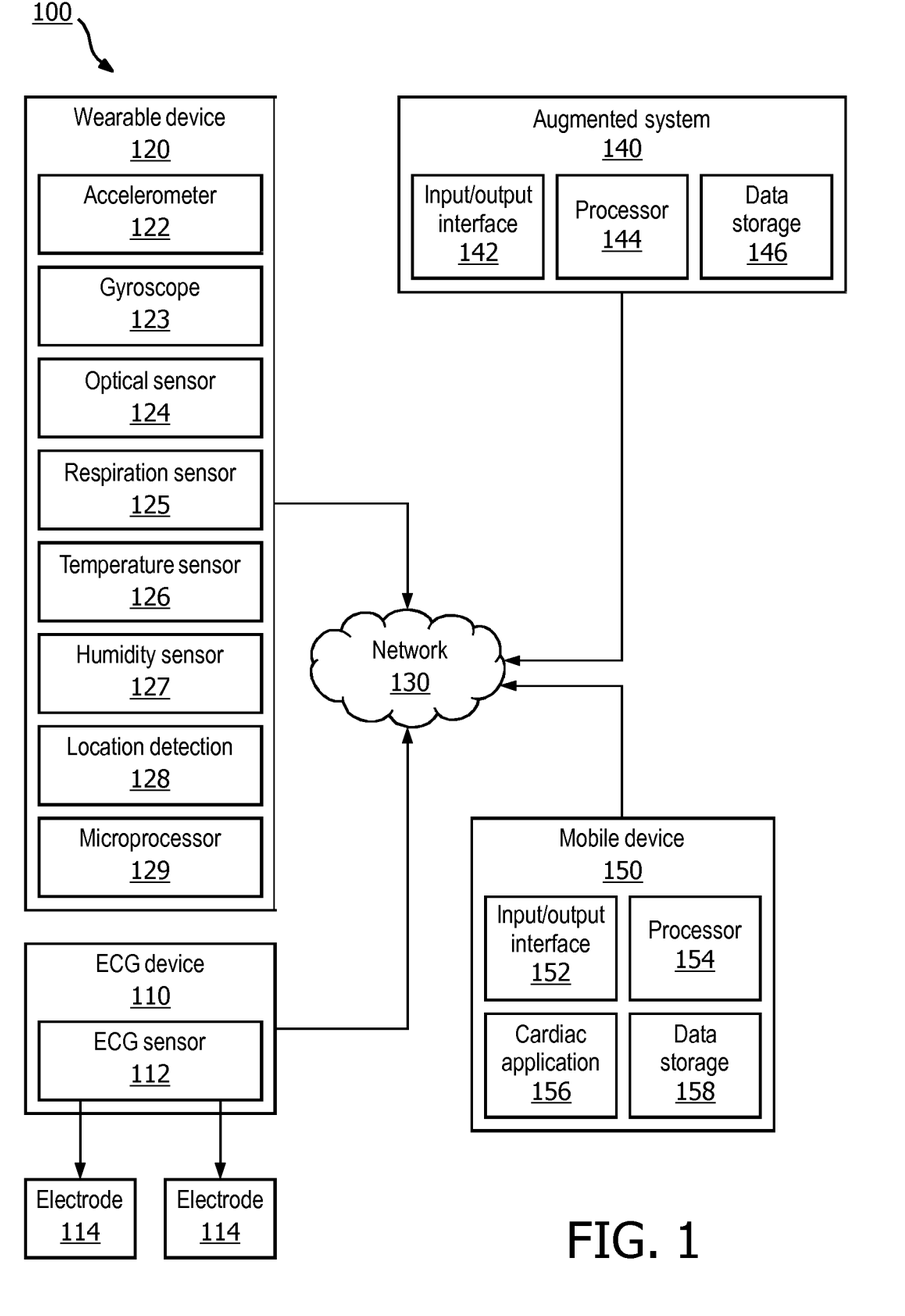
FIG. 1 depicts an example embodiment of an environment in which a cardiac/non-cardiac pain detection system operates.

FIG. 1 depicts an exemplary system 100 for use with the device, system, and method for detecting pain in a cardiac-related region of the body and determining whether that pain is cardiac or non-cardiac related. As shown in FIG. 1, an example system 100 may include one or more ECG devices 110, one or more wearable devices 120, one or more augmented systems 140, and/or one or more mobile devices 150 connected over one or more networks 130.

For example, network 130 may be one or more of a wireless network, a wired network or any combination of wireless network and wired network. For example, network 130 may include one or more of a fiber optics network, a passive optical network, a cable network, an Internet network, a satellite network, a wireless LAN, a Global System for Mobile Communication ("GSM"), a Personal Communication Service ("PCS"), a Personal Area Network ("PAN"), Wireless Application Protocol (WAP), Multimedia Messaging Service (MMS), Enhanced Messaging Service (EMS), Short Message Service (SMS), Time Division Multiplexing (TDM) based systems, Code Division Multiple Access (CDMA) based systems, D-AMPS, Wi-Fi, Fixed Wireless Data, IEEE 802.11b, 802.15.1, 802.11n and 802.11g, a Bluetooth network, or any other wired or wireless network for transmitting and receiving a data signal.

In addition, network 130 may include, without limitation, telephone lines, fiber optics, IEEE Ethernet 902.3, a wide area network ("WAN"), a local area network ("LAN"), a wireless personal area network ("WPAN"), or a global network such as the Internet. Also network 130 may support an Internet network, a wireless communication network, a cellular network, or the like, or any combination thereof. Network 130 may further include one network, or any number of the example types of networks mentioned above, operating as a stand-alone network or in cooperation with each other. Network 130 may utilize one or more protocols of one or more network elements to which they are communicatively coupled. Network 130 may translate to or from other protocols to one or more protocols of network devices. Although network 130 is depicted as a single network, it should be appreciated that according to one or more embodiments, network 130 may comprise a plurality of interconnected networks, such as, for example, the Internet, a service provider's network, a cable television network, corporate networks, and home networks.

ECG device 110 may include one or more ECG sensors 112 connectively coupled to one or more electrodes 114. Although wearable device 120 and ECG device 110 are depicted as separate devices, it should be appreciated that the device components may be combined to form a singular device. Wearable device 120 may include, for example, an accelerometer 122, a gyroscope 123, one or more optical sensors 124, one or more respiration sensors 125, one or more temperature sensors 126, one or more humidity sensors 127, location-detection technology 128, and/or one or more microprocessors 129. A respiration sensor 125 may include, for example, mechanical, expansion-related sensors and/or electrical, impedance-related sensors. An optical sensor 124 may be used, for example, to measure heartrate, temperature, $SpO_2$ levels, $PO_2$ levels, $PCO_2$ levels, and/or glucose levels.

A wearable device 120 may, for example, detect activity levels such as a number of steps taken, a heartrate, a number of floors climbed, a type of activity, a distance a user has moved, and/or the like. Using raw data captured on a wearable device 120, an activity level may be determined and classified. Activity levels may include a low activity level, a moderate activity level, and a high activity level. A wearable device 120 may be a limb-worn device (e.g., wrist, arm, ankle, leg), a chest-worn device, and/or a multi-location worn device. In various embodiments, an ECG device 110 and/or wearable device 120 may comprise a wireless patch, a wired patch, a limb-worn device, and/or an implantable device.

Augmented system 140 may include an input/output interface 142, a processor 144, and/or data storage 146. Although augmented system 140 is depicted as a standalone system, augmented system 140 may be incorporated into, for example a wearable device 120 and/or a mobile device 150.

Augmented system 140 and/or mobile device 150 may include, for example, one or more mobile devices, such as, for example, personal digital assistants (PDA), tablet computers and/or electronic readers (e.g., iPad, Kindle Fire, Playbook, Touchpad, etc.), wearable devices (e.g., Google Glass), telephony devices, smartphones, cameras, music playing devices (e.g., iPod, etc.), televisions, set-top-box devices, and the like. Augmented system 140 and/or mobile device 150 also may include a network-enabled computer system and/or device. As referred to herein, a network-enabled computer system and/or device may include, but is not limited to: e.g., any computer device, or communications device including, e.g., a server, a network appliance, a personal computer (PC), a workstation, a mobile device, a phone, a handheld PC, a personal digital assistant (PDA), a thin client, a fat client, an Internet browser, or other device. The network-enabled computer systems may execute one or more software applications (e.g., cardiac application 156) to, for example, receive data as input from an entity accessing the network-enabled computer system, process received data, transmit data over a network, and receive data over a network.

Augmented system 140 and/or mobile device 150 may include at least one central processing unit (CPU), which may be configured to execute computer program instructions to perform various processes, methods and/or modules. As used herein, the term "module" may be understood to refer to computer executable software, firmware, hardware, and/or various combinations thereof. It is noted there where a module is a software and/or firmware module, the module is configured to affect the hardware elements of an associated system. It is further noted that the modules shown and described herein are intended as examples. The modules may be combined, integrated, separated, or duplicated to support various applications. Also, a function described herein as being performed at a particular module may be performed at one or more other modules and by one or more other devices instead of or in addition to the function performed at the particular module. Further, the modules may be implemented across multiple devices or other components local or remote to one another. Additionally, the modules may be moved from one device and added to another device, or may be included in both devices.

Augmented system 140 and/or mobile device 150 may include an input/output interface 142, 152. Input/output interface 142, 152 also may include antennas, network interfaces that may provide or enable wireless and/or wire line digital and/or analog interface to one or more networks, such as network 130, over one or more network connections, a power source that provides an appropriate alternating current (AC) or direct current (DC) to power one or more components of system 100, and a bus that allows communication among the various components of system 100. Input/output interface 142, 152 may include a display, which may include for example output devices, such as a printer, display screen (e.g., monitor, television, and the like), speakers, projector, and the like. Although not shown, input/output interface 142, 152 may include one or more encoders and/or decoders, one or more interleavers, one or more circular buffers, one or more multiplexers and/or de-multiplexers, one or more permuters and/or depermuters, one or more encryption and/or decryption units, one or more modulation and/or demodulation units, one or more arithmetic logic units and/or their constituent parts, and/or the like.

Input/output interface 142, 152 may include a Bluetooth module or chipset with a Bluetooth transceiver, a chip, and an antenna. The transceiver may transmit and receive information via the antenna and an interface. The chip may include a microprocessor that stores and processes information specific to a piconet and provides device control functionality. Device control functionality may include connection creation, frequency-hopping sequence selection and timing, power control, security control, polling, packet processing, and the like. The device control functionality and other Bluetooth-related functionality may be supported using a Bluetooth API provided by the platform associated with the augmented system 140 and/or mobile device 150.

Using a Bluetooth API, an application stored on augmented system 140 and/or mobile device 150 may be able to scan for other Bluetooth devices, query the local Bluetooth adapter for paired Bluetooth devices, establish RFCOMM channels, connect to other devices through service discovery, transfer data to and from other devices, and manage multiple connections. A Bluetooth API used in the methods, systems, and devices described herein may include an API for Bluetooth Low Energy (BLE) to provide significantly lower power consumption and allow an augmented system 140 and/or mobile device 150 to communicate with BLE devices that have low power requirements (e.g., ECG device 110 and/or wearable device 120).

Input/output module 142, 152 may also include an NFC antenna and secure element (SE). In one embodiment, the SE may be used for digitally and physically secure storage of sensitive data. The SE may include a computer processor or other computational hardware or software. A secure element may take the form of a universal integrated circuit card (UICC) and/or a microSD card. A UICC may identify a user to a wireless operator, store contacts, enable secure connections, and add new applications and services.

Input/output module 142, 152 may enable Industry Standard NFC Transmission. For example, the input/output module 142, 152 may enable two loop antennas to form an air-core transformer when placed near one another by using magnetic induction. Input/output module 142, 152 may operate at 13.56 MHz or any other acceptable frequency. Also, input/output module 142, 152 may provide for a passive communication mode, where the initiator device provides a carrier field, permitting answers by the target device via modulation of existing fields. Additionally, input/output module 142, 152 also may provide for an active communication mode by allowing alternate field generation by the initiator and target devices.

Input/output module 142, 152 may deactivate the RF field while awaiting data. The attachment may use Miller-type coding with varying modulations, including 100% modulation. The attachment may also use Manchester coding with varying modulations, including a modulation ratio of 10%. Additionally, the attachment may be capable of receiving and transmitting data at the same time, as well as checking for potential collisions when the transmitted signal and received signal frequencies differ.

Input/output module 142, 152 may be capable of utilizing standardized transmission protocols. Also, input/output module 142, 152 may be able to utilize transmission protocols and methods that are developed in the future using other frequencies or modes of transmission. Input/output module 142, 152 may also be backwards-compatible with existing techniques, for example RFID.

Augmented system 140 and/or mobile device 150 may include data storage 146, 158, including for example, random access memory (RAM) and read only memory (ROM), which may be configured to access and store data and information and computer program instructions. Data storage 146, 158 may also include storage media or other suitable type of memory (e.g., such as, for example, RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives, any type of tangible and non-transitory storage medium), where the files that comprise an operating system, application programs including, for example, web browser application, email application and/or other applications, and data files may be stored. Data storage 146, 158 may include electronic information, files, and documents stored in various ways, including, for example, a flat file, indexed file, hierarchical database, relational database, such as a database created and maintained with software from, for example, Oracle® Corporation, Microsoft® Excel file, Microsoft® Access file, or any other storage mechanism. Augmented system 140 and/or mobile device 150 may further include, for example, a processor 144, 154, which may be several processors, a single processor, or a single device having multiple processors. Processor 144, 154 may include any range of processing, such as, for example a one-chip microprocessor or a multi-chip processing unit. In various embodiments, processor 144 and/or processor 154 may execute a number of instructions and/or modules.

Augmented system 140 and/or mobile device 150 may include any mobile device running the Apple® iOS operating system (e.g., iPhone, iPad, Apple Watch, and/or the like) and/or any device running Google's Android® operating system, including, for example, smartphones running the Android® operating system and other wearable mobile devices, such as Google Glass or Samsung Galaxy Gear Smartwatch, any device running Microsoft's Windows® Mobile operating system, and/or any other smartphone or like device.

Although not shown, mobile device 150, augmented system 140, ECG device 110 and/or wearbale device 120 may connect to a system associated with a general practitioner and/or specialist over network 130 in order to transmit any received data and/or measurements associated with the monitoring described herein.

Figure 3:
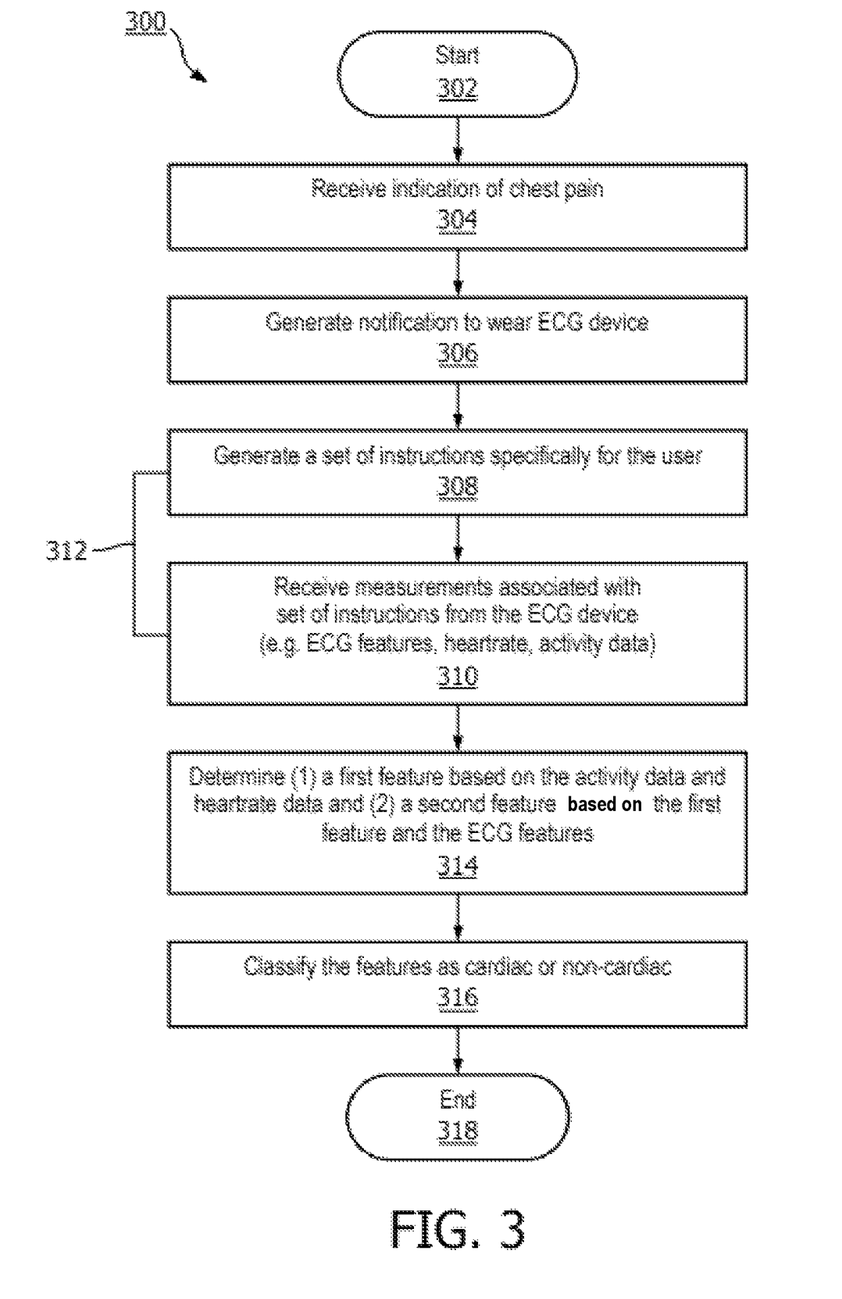
FIG. 3 depicts a flow diagram that illustrates an example method to determine cardiac and non-cardiac pain in accordance with an embodiment of the invention.

With reference to FIG. 3, a method 300 that utilizes, for example, the system components of FIG. 1 may begin at block 302. This method may include received measurements and/or raw data from a wearable and/or an ECG device in order to derive specific features. In various embodiments, the wearable device and the ECG device are the same device. In various embodiments, the wearable device and the ECG device are separate devices. In various embodiments, each input received may be received via the same device.

At block 304, an ECG device 110, wearable device 120, augmented system 140, and/or mobile device 150 may receive an indication of chest pain along with pain details. For example, as used herein the term "data indicative of chest pain" includes receiving an indication of one or more of the following data: an anatomical region associated with pain, a type of pain (e.g., severe, moderate, mild, throbbing, sharp, aching, tingling, sudden, constant, squeezing, heaviness, substernal (location) pain radiating to left arm or jaw, associated with sweating and/or the like), and/or details associated with the chest pain (e.g., time of pain onset, duration of pain, activity surrounding onset, geographical location of onset, weather associated with the geographical location of onset, and/or the like). This first input may be received on a user's mobile device via user input and/or third party system input (e.g., GPS data, weather data via third-party weather provider, time data via system clock, and/or the like).

At block 306, a system may generate a notification to wear an ECG device and/or a wearable device. This notification may include instructions to wear an ECG device and/or other wearable device for a predefined amount of time (e.g., one minute, two minutes, three minutes five minutes, ten minutes, and/or the like) upon received an indication of chest pain. At block 308, a system may generate a set of instructions for the user/wearer. A set of instructions may be user-specific based on known medical conditions, diagnosis, and/or monitored vital sign data. By way of example, a set of instructions may include a set of instructions for moderate exercise (e.g., brisk walking, biking, swimming, or the like), a set of instructions for increased difficulty of exercise (e.g., jogging, increasing a walking incline, increasing speed, incline, and/or resistance for biking, increasing speed and/or resistance for swimming, jumping rope, and/or the like), a set of instructions for cool down exercises (e.g., walking, stretching, breathing exercises, and/or the like), and/or any combination thereof. Where a set of instructions includes varying difficulty (e.g., speed, incline, resistance, type of exercise, and/or the like), each level of difficulty may be assigned a particular amount of time.

A set of instructions, feedback, and/or notifications described herein may include audio instructions, visual instructions (e.g., video, a set of symbols, LED lighting and/or patterns, textual instructions), and/or tactile feedback instructions. A set of instructions, feedback, and/or may be provided in the form of a push notification, a text, and/or a voice message.

The amount of time, level of difficulty, and/or type of exercise may be dynamically altered based on feedback and/or measurements received from an ECG device and/or a wearable device, such as ECG device 110 and/or wearable device 120, such as in steps 310 and 312.

At block 310, a system and/or device, such as an augmented system 140 and/or a mobile device 150, may receive real-time measurements associated with the set of instructions from an ECG device and/or a wearable device, such as ECG device 110 and/or wearable device 120. These measurements may be received via wired and/or wireless channels such as those described herein. Where additional measurements are needed and/or exercises vary, an additional set of instructions may be re-generated at step 312.

At blocks 314 and 316, a system and/or device, such as augmented system 140 and/or mobile device 150, may determine whether the real-time measurements associated with the set of instructions are cardiac or non-cardiac as described herein.

Figure 2A:
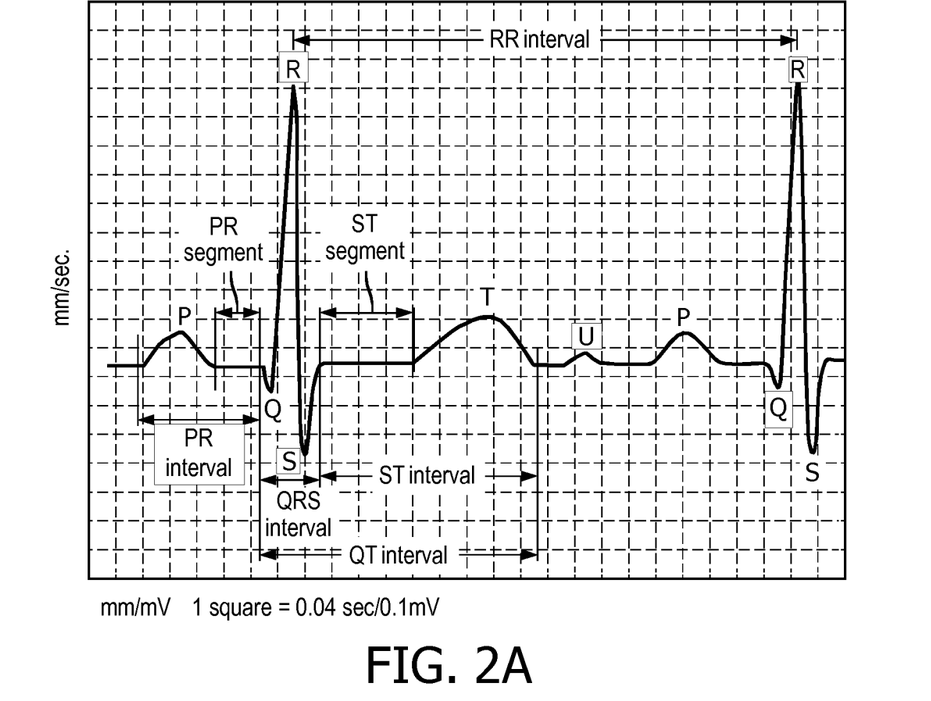
FIGS. 2A and 2B are chart diagrams that respectively illustrate a typical ECG signal along with fiducial points and extraction of morphological structure using curve fitting.
Figure 2B:
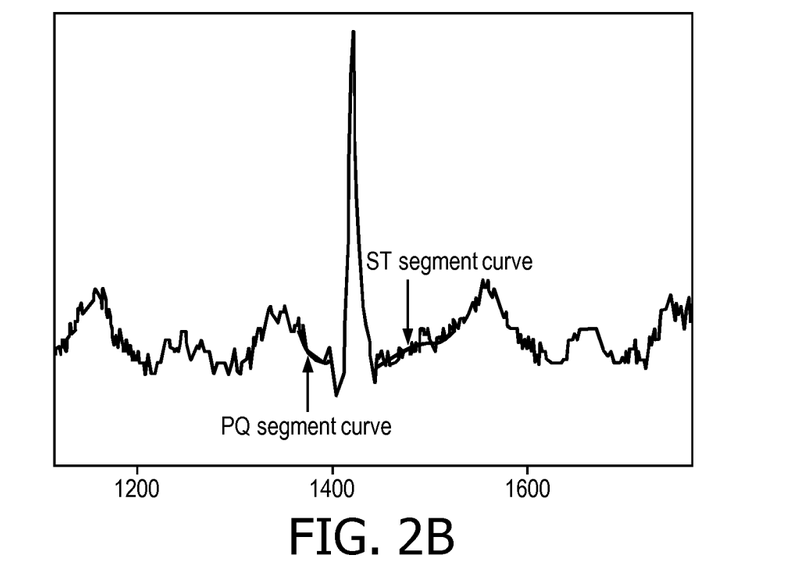

For example, with reference to FIGS. 2A and 2B, and ECG device, similar to ECG device 110, may extract ECG-based features. For example, an ECG device may collect ECG data and apply an adaptive band pass filter, thereby eliminating the baseline wander and interference data. The ECG device may identify all fiducial points in a given segment. The ECG device may perform a fragment analysis on the ECG data.

For example, with reference to FIG. 2A, in R-R interval, an inversion of T peak, distance between different fiducial points may be computed, which acts as a feature set of data. In addition, an ECG device may perform cubic spline fitting on the ST and PQ segments. Principal components may then be extracted by performing Karhunun Loeve Transform (KLT) on the fitted curve. The signal may then be conditioned to remove noise and power line interference. Adaptive band pass filter in, for example, the frequency range of 0.04 Hz-150 Hz may be used to extract relevant signals from the ECG data. The adaptive filter may include a single pole and a single zero, as follows:

$$H_k(n, z) = \frac{b_k(n) + c_k(n)z^{-1}}{1 - a_k(n)z^{-1}} \quad (1)$$

Where $\{a_k, b_k, c_k\}$ are adaptive filter coefficients. Hk may be the transfer function.

The conditioned signal may be fed to a fiducial point identification algorithm to detect P, Q, R, S, and T points in the ECG waveform. The R peak being prominent in the ECG may be initially identified using the frequency domain approach. The frequency domain may be a transformed ECG signal obtained as:

$$x_H(t) = \text{IFT}\{\text{FT}[x(t)]H(f)\} \quad (2)$$

where x(t) is an input ECG signal and FT and IFT represented Fourier and inverse Fourier transform, respectively, and $$H(f) = \begin{cases} -j & 0 < f < \pi \\ j, & -\pi < f < 0 \end{cases} \quad (3)$$

In various embodiments, a threshold may be employed on a frequency domain transformed ECG signal to identify the peaks that are mapped back to the original signal for identification of R peaks. The first lowest minimum on the left and right side of the R peak may form the Q and/or S point, and the time window of the search of Q and S with respect to R may be empirically defined.

In various embodiments, to determine a P wave, a time window may be set prior to beginning the QRS complex fiducial and the QRS onset to the beginning of the heartbeat. The fiducial point may then be determined by searching a first isoelectric sample prior to the start of atrial deflection. To detect P waves, for example, a delineator may compute the slope threshold, which may be obtained using a first derivative approach. For example, the first derivative of the ECG, y(nT), at time instant T is calculated using the following time difference equation, with N being the length of time of the sample.

$$y(nT) = \frac{x(nT - (N-1)T) + x(nT - (N-2)T) + \cdots + x(nT))}{N} \quad (4)$$

The zero crossing of the differentiated signal may map to the P peak and succeeding the lowest crest on the differentiated signal maps to the P offset. A similar approach may be followed to determine the T peak by considering the segment after point S.

With reference to FIG. 2B, using an analysis of the maximum frequency envelope, there may exist a change in morphological stricter in the downward sloping sections of the ST and PQ segments during cardiac pain. Accordingly, the curve may be fit (cubic spline) on these segments as illustrated in FIG. 2B and Karhunun Loeve Transform (KLT) may be applied to the fitted curve. The KLT operation may reveal an internal structure of data to explain data variance. Additionally, after applying KLT and obtaining principal component vales, the principal component values may act as the feature set for cardiac/non-cardiac classification.

By way of example, if $X_i$ is a sample data vector fit on the ST or PQ segment, a covariance matrix of the data may be computed as follows:

$$C = \frac{1}{n}\sum_{i=1}^{n} X_i X_i^T \quad (5)$$

where C is the covariance matric, $X_i$ is a sample data vector of a fitted segment on the ECG and n is the number of samples. Furthermore, Eigen value decomposition may be performed on the covariance matrix C. The vectors associated with the corresponding Eigen value (i.e., the principal values) may be considered as the feature set. Additional features that may be extracted from the fragment analysis may include the time interval from R peak to P off-set and P peak, the time interval from R peak to S, and the time interval from S to J point. Similar feature vectors may be extracted from the PQ segment.

Other features beyond ECG features may be derived from a wearable device, such as wearable device 120. For example, activity level-based features may be derived, such as: the mean value of different activity levels in terms of distance covered and/or step count computed per interval (e.g., per minute, per 30 seconds, per 15 seconds, and/or the like); the moving average of different activity levels in terms of distance covered and/or step count per a time period (e.g., at time t, the feature may be an average between t to t−10 minutes estimated at an interval of every minute), an estimated active time for a particular interval and/or entire instruction time (e.g., every minute, every 2 minutes, every 3 minutes, every 5 minutes, every 10 minutes and/or the like), a moving average of variation of different activities updated periodically (e.g., every minute, every 2 minutes, every 3 minutes, every 5 minutes, every 10 minutes, and/or the like) for a specific interval (e.g., every minute, every 2 minutes, every 3 minutes, every 5 minutes, every 10 minutes, and/or the like), and/or the moving average of a variation in active time (e.g., at time t, the moving average is an average heartrate variability between t to t−10 minutes).

Additionally, heartrate-based features may be derived, such as, the variability of the heartrate at a particular interval (e.g., every minute, every 2 minutes, every 3 minutes, every 5 minutes, every 10 minutes, and/or the like) and/or the moving average of variation in heartrate updated periodically (e.g., every minute, every 2 minutes, every 3 minutes, every 5 minutes, every 10 minutes, and/or the like) for a particular interval (e.g., every minute, every 2 minutes, every 3 minutes, every 5 minutes, every 10 minutes, and/or the like).

Once the various features (e.g., ECG features, activity level-based features, and/or heartrate-based features) are extracted and/or derived, additional features may be computed (e.g., quantitative features) based on the extracted features. For example, at block 314, a first and a second feature may each be determined and/or calculated. Table 1 below illustrates a first feature, W1 that may be an assigned or computed weight or value such as w10 (initial weight or value), w11, or w12, where w12>w11. The first feature may be computed based on activity level- and heartrate-based features. This feature captures the correlation between variation in activity level and corresponding heartrates.

TABLE 1

| Variation in Activity Level | Variation in Heartrate | Feature ($W_1$) |
| --- | --- | --- |
| No | No | $w_{10}$ |
| Yes (increase) | No | $w_{10}$ |
| Yes (decrease) | No | $w_{10}$ |
| Yes (increase) | Yes (increase) | $w_{11}$ |
| Yes (increase) | Yes (decrease) | $w_{11}$ |
| Yes (decrease) | Yes (increase) | $w_{12}$ |
| Yes (decrease) | Yes (decrease) | $w_{11}$ |

Table 2 illustrate a second feature, $W_2$, that may be an assigned or computed weight or value such as $w_{20}$ (initial second feature weight or value), $w_{21}$, or $w_{22}$, where $w_{22}>w_{21}$. A second feature may be computed or assigned based on the first feature $W_1$ and a variation or correlation between ECG features. The second feature $W_2$ may capture the correlation in variation of changes in activity levels, heart rate and/or corresponding ECG features.

A variation in ECG features, such as the features described herein, may be determined by computing a distance between two successive measurements, where the existence of a variation is based on a predefined threshold. A variation in ECG may be determined by computing a Euclidean distance between the features.

TABLE 2

| Variation in ECG Features | $W_1$ | Feature ($W_2$) |
| --- | --- | --- |
| No | $W_{10}$ | $W_{20}$ |
| Yes | $W_{11}$ | $W_{21}$ |
| Yes | $W_{12}$ | $W_{22}$ |

At block 316, all the above features (e.g., $W_1$, $W_2$, ECG features) may then be subject to a support vector machine (SVM) classifier to determine whether the underlying data indicates pain is cardiac or non-cardiac. In an SVM classifier, the features may be nonlinearly mapped to a higher dimension features space where a linear separation surface may be created to separate the training data by minimizing the margin between the vectors of the two classes. Separation may be achieved by the decision surface with the largest distance to the nearest training data point of any class, where each subspace corresponds to one class of the training data.

Once the training is complete, test data may be mapped to the feature space. A class may then be assigned to the test data depending on which subspace the data is mapped to. The features in the input space may be transformed to a higher dimensional space where they may then be used for calculating a maximum margin hyperplane iteratively that provides the best performance.

Accordingly, this classifier may construct a decision function, $f:RN \rightarrow \{\pm 1\}$, using the given N-dimensional training data. Assuming a dataset represented by $(x_1, y_1)$, $(x_2, y_2)$, ... $(x_i, y_i) \in R^N\{\pm 1\}$ where $x_1$ and $y_1$ represent features vectors and class labels, respectively. The hyperplane in multidimensional space may be defined by a linear discriminant function given by $g(x)=W^T x+\omega_0$, where x is the feature vector W is the weight vector orthogonal to the decision hyperplane and $\omega_0$ is the threshold. Weights and/or threshold parameters may be optimized for each type of activity during the model training phase.

Where a classifier indicates cardiac pain, a notification may be received via a wearable device and/or mobile devices associate with the user such that the user is notified to seek medical attention as early as possible. An augmented system, wearable device, and/or mobile device may transmit received ECG recording data to a general practice (GP), emergency care, and/or other medical professional.

The method may end at block 318.

Figure 4:
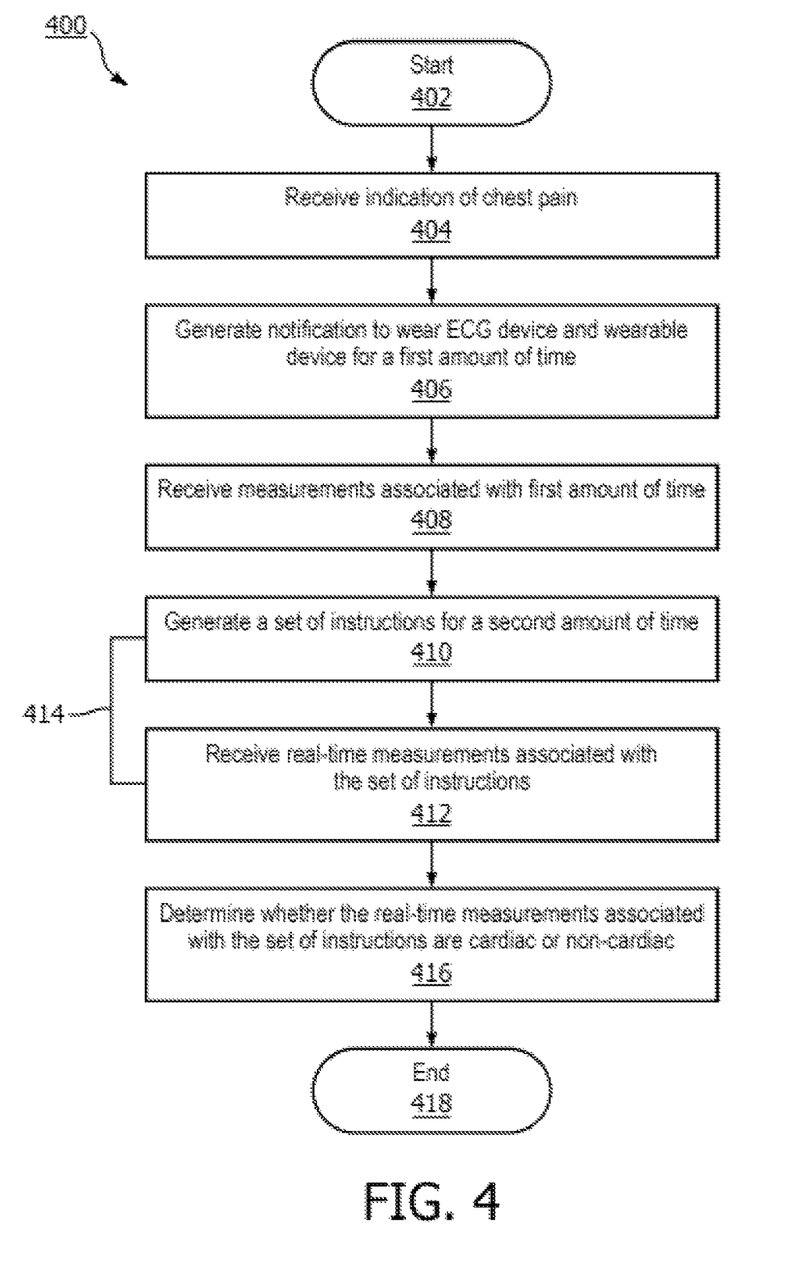
FIG. 4 depicts a flow diagram that illustrates an example method to determine cardiac and non-cardiac pain in accordance with an embodiment of the invention.

With reference to FIG. 4, a method 400 that utilizes the system components of FIG. 1 may begin at block 402. This method may include received measurements and/or raw data from a wearable and/or an ECG device in order to derive specific features. In various embodiments, the wearable device and the ECG device are the same device. In various embodiments, the wearable device and the ECG device are separate devices. In various embodiments, each input received may be received via the same device.

At block 404, an ECG device 110, wearable device 120, augmented system 140, and/or mobile device 150 may receive an indication of chest pain along with pain details. For example, this indication of chest pain may include receiving an indication of: an anatomical region associated with pain, a type of pain (e.g., severe, moderate, mild, throbbing, sharp, aching, tingling, sudden, constant, squeezing, heaviness, substernal (location) pain radiating to left arm or jaw, associated with sweating and/or the like), and/or details associated with the chest pain (e.g., time of pain onset, duration of pain, activity surrounding onset, geographical location of onset, weather associated with the geographical location of onset, and/or the like). This first input may be received on a user's mobile device via user input and/or third party system input (e.g., GPS data, weather data via third-party weather provider, time data via system clock, and/or the like).

At block 406, a system may generate a notification to wear an ECG device and/or a wearable device for a first amount of time (e.g., one minute, two minutes, three minutes five minutes, ten minutes, and/or the like) upon received an indication of chest pain. At block 408, a system may receive ECG measurements associated with that first amount of time to determine an acute ischemic change based on the received first input. Acute ischemic changes are usually seen in ST segment, as either ST depression or ST elevation. If the baseline (resting) ECG already has some ST changes then the changes in the Exercise ECG is compared with the Baseline ECG. If acute ischemic changes in ECG are detected a notification may be received via a wearable device and/or mobile devices associate with the user such that the user is notified to seek medical attention as early as possible. An augmented system, wearable device and/or mobile device may transmit received ECG recording data to a general practice (GP), emergency care, and/or other medical professional.

At block 410, a system may generate a set of instructions. This set of instructions may be a set of instructions for a second amount of time. By way of example, a set of instructions may include a set of instructions for moderate exercise (e.g., brisk walking, biking, swimming, or the like), a set of instructions for increased difficulty of exercise (e.g., jogging, increasing a walking incline, increasing speed, incline, and/or resistance for biking, increasing speed and/or resistance for swimming, jumping rope, and/or the like), a set of instructions for cool down exercises (e.g., walking, stretching, breathing exercises, and/or the like), and/or any combination thereof. Where a set of instructions includes varying difficulty (e.g., speed, incline, resistance, type of exercise, and/or the like), each level of difficulty may be assigned a particular amount of time.

A set of instructions, feedback, and/or notifications described herein may include audio instructions, visual instructions (e.g., video, a set of symbols, LED lighting and/or patterns, textual instructions), and/or tactile feedback instructions. A set of instructions, feedback, and/or may be provided in the form of a push notification, a text, and/or a voice message.

The amount of time, level of difficulty, and/or type of exercise may be dynamically altered based on feedback and/or measurements received from an ECG device and/or a wearable device, such as ECG device 110 and/or wearable device 120, such as in steps 412 and 414.

At block 412, a system and/or device, such as an augmented system 140 and/or a mobile device 150, may receive real-time measurements associated with the set of instructions from an ECG device and/or a wearable device, such as ECG device 110 and/or wearable device 120. These measurements may be received via wired and/or wireless channels such as those described herein. Where additional measurements are needed and/or exercises vary, an additional set of instructions may be re-generated at step 414.

At block 416, a system and/or device, such as augmented system 140 and/or mobile device 150, may determine whether the real-time measurements associated with the set of instructions are cardiac or non-cardiac as described herein.

For example, with reference to FIGS. 2A and 2B, and ECG device, similar to ECG device 110, may extract ECG-based features. For example, an ECG device may collect ECG data and apply an adaptive band pass filter, thereby eliminating the baseline wander and interference data. The ECG device may identify all fiducial points in a given segment. The ECG device may perform a fragment analysis on the ECG data.

For example, with reference to FIG. 2A, in R-R interval, an inversion of T peak, distance between different fiducial points may be computed, which acts as a feature set of data. In addition, an ECG device may perform cubic spline fitting on the ST and PQ segments. Principal components may then be extracted by performing Karhunun Loeve Transform (KLT) on the fitted curve. The signal may then be conditioned to remove noise and power line interference. Adaptive band pass filter in, for example, the frequency range of 0.04 Hz-150 Hz may be used to extract relevant signals from the ECG data. They adaptive filter may include a single pole and a single zero, as follows:

$$H_k(n,z) = \frac{b_k(n) + c_k(n)z^{-1}}{1 - a_k(n)z^{-1}} \quad (1)$$

Where $\{a_k, b_k, c_k\}$ are adaptive filter coefficients. $H_k$ may be the transfer function.

The conditioned signal may be fed to a fiducial point identification algorithm to detect P, Q, R, S, and T points in the ECG waveform. The R peak being prominent in the ECG may be initially identified using the frequency domain approach. The frequency domain may be a transformed ECG signal obtained as:

$$x_H(t) = \text{IFT}\{\text{FT}[x(t)]H(f)\} \quad (2)$$

where x(t) is an input ECG signal and FT and IFT represented Fourier and inverse Fourier transform, respectively, and $$H(f) = \begin{cases} -j \; 0 < f < \pi \\ j, \; -\pi < f < 0 \end{cases} \quad (3)$$

In various embodiments, a threshold may be employed on a frequency domain transformed ECG signal to identify the peaks that are mapped back to the original signal for identification of R peaks. The first lowest minimum on the left and right side of the R peak may form the Q and/or S point, and the time window of the search of Q and S with respect to R may be empirically defined.

In various embodiments, to determine a P wave, a time window may be set prior to beginning the QRS complex fiducial and the QRS onset to the beginning of the heartbeat. The fiducial point may then be determined by searching a first isoelectric sample prior to the start of atrial deflection. To detect P waves, for example, a delineator may compute the slope threshold, which may be obtained using a first derivative approach. For example, the first derivative of the ECG, y(nT), at time instant T is calculated using the following time difference equation, with N being the length of time of the sample.

$$y(nT) = \frac{x(nT - (N-1)T) + x(nT - (N-2)T) + \cdots + x(nT))}{N} \quad (4)$$

The zero crossing of the differentiated signal may map to the P peak and succeeding the lowest crest on the differentiated signal maps to the P offset. A similar approach may be followed to determine the T peak by considering the segment after point S.

With reference to FIG. 2B, using an analysis of the maximum frequency envelope, there may exist a change in morphological stricter in the downward sloping sections of the ST and PQ segments during cardiac pain. Accordingly, the curve may be fit (cubic spline) on these segments as illustrated in FIG. 2B and Karhunun Loeve Transform (KLT) may be applied to the fitted curve. The KLT operation may reveal an internal structure of data to explain data variance. Additionally, after applying KLT and obtaining principal component vales, the principal component values may act as the feature set for cardiac/non-cardiac classification.

By way of example, if $X_i$ is a sample data vector fit on the ST or PQ segment, a covariance matrix of the data may be computed as follows:

$$C = \frac{1}{n} \sum_{i=1}^{n} X_i X_i^T \quad (5)$$

where C is the covariance matric, $X_i$ is a sample data vector of a fitted segment on the ECG and n is the number of samples. Furthermore, Eigen value decomposition may be performed on the covariance matrix C. The vectors associated with the corresponding Eigen value (i.e., the principal values) may be considered as the feature set. Additional features that may be extracted from the fragment analysis may include the time interval from R peak to P off-set and P peak, the time interval from R peak to S, and the time interval from S to J point. Similar feature vectors may be extracted from the PQ segment.

Other features beyond ECG features may be derived from a wearable device, such as wearable device 120. For example, activity level-based features may be derived, such as: the mean value of different activity levels in terms of distance covered and/or step count computed per interval (e.g., per minute, per 30 seconds, per 15 seconds, and/or the like); the moving average of different activity levels in terms of distance covered and/or step count per a time period (e.g., at time t, the feature may be an average between t to t–10 minutes estimated at an interval of every minute), an estimated active time for a particular interval and/or entire instruction time (e.g., every minute, every 2 minutes, every 3 minutes, every 5 minutes, every 10 minutes and/or the like), a moving average of variation id different activities updated periodically (e.g., every minute, every 2 minutes, every 3 minutes, every 5 minutes, every 10 minutes, and/or the like) for a specific interval (e.g., every minute, every 2 minutes, every 3 minutes, every 5 minutes, every 10 minutes, and/or the like), and/or the moving average of a variation in active time (e.g., at time t, the moving average is an average heartrate variability between t to t–10 minutes).

Additionally, heartrate-based features may be derived, such as, the variability of the heartrate at a particular interval (e.g., every minute, every 2 minutes, every 3 minutes, every 5 minutes, every 10 minutes, and/or the like) and/or the moving average of variation in heartrate updated periodically (e.g., every minute, every 2 minutes, every 3 minutes, every 5 minutes, every 10 minutes, and/or the like) for a particular interval (e.g., every minute, every 2 minutes, every 3 minutes, every 5 minutes, every 10 minutes, and/or the like).

Once the various features (e.g., ECG features, activity level-based features, and/or heartrate-based features) are extracted and/or derived, additional features may be computed based on the extracted features. For example, Table 1 below illustrates a first feature, $W_1$ that may be an assigned or computed weight or value such as $w_{10}$ (initial weight or value), $w_{11}$, or $w_{12}$, where $w_{12} > w_{11}$. The first feature may be computed based on activity level- and heartrate-based features. This feature captures the correlation between variation in activity level and corresponding heartrates.

TABLE 1

| Variation in Activity Level | Variation in Heartrate | Feature ($W_1$) |
|---|---|---|
| No | No | $w_{10}$ |
| Yes (increase) | No | $w_{10}$ |
| Yes (decrease) | No | $w_{10}$ |
| Yes (increase) | Yes (increase) | $w_{11}$ |
| Yes (increase) | Yes (decrease) | $w_{11}$ |
| Yes (decrease) | Yes (increase) | $w_{12}$ |
| Yes (decrease) | Yes (decrease) | $w_{11}$ |

Table 2 illustrate a second feature, $W_2$, that may be an assigned or computed weight or value such as $w_{20}$ (initial second feature weight or value), $w_{21}$, or $w_{22}$, where $w_{22} > w_{21}$. A second feature may be computed or assigned based on the first feature $W_1$ and a variation or correlation between ECG features. The second feature $W_2$ may capture the correlation in variation of changes in activity levels, heart rate and/or corresponding ECG features.

A variation in ECG features, such as the features described herein, may be determined by computing a distance between two successive measurements, where the existence of a variation is based on a predefined threshold. A variation in ECG may be determined by computing a Euclidean distance between the features.

TABLE 2

| Variation in ECG Features | $W_1$ | Feature ($W_2$) |
|---|---|---|
| No | $W_{10}$ | $W_{20}$ |
| Yes | $W_{11}$ | $W_{21}$ |
| Yes | $W_{12}$ | $W_{22}$ |

All the above features (e.g., $W_1$, $W_2$, ECG features) may then be subject to a support vector machine (SVM) classifier to determine whether the underlying data indicates pain is cardiac or non-cardiac. In an SVM classifier, the features may be nonlinearly mapped to a higher dimension features space where a linear separation surface may be created to separate the training data by minimizing the margin between the vectors of the two classes. Separation may be achieved by the decision surface with the largest distance to the nearest training data point of any class, where each subspace corresponds to one class of the training data.

Once the training is complete, test data may be mapped to the feature space. A class may then be assigned to the test data depending on which subspace the data is mapped to. The features in the input space may be transformed to a higher dimensional space where they may then be used for calculating a maximum margin hyperplane iteratively that provides the best performance.

Accordingly, this classifier may construct a decision function, $f:RN \rightarrow \{\pm 1\}$, using the given N-dimensional training data. Assuming a dataset represented by $(x_1, y_1)$, $(x_2, y_2)$, ... $(x_i, y_i) \in R^N\{\pm 1\}$ where $x_1$ and $y_1$ represent features vectors and class labels, respectively. The hyperplane in multidimensional space may be defined by a linear discriminant function given by $g(x)=W^T x+\omega_0$, where x is the feature vector W is the weight vector orthogonal to the decision hyperplane and $\omega_0$ is the threshold. Weights and/or threshold parameters may be optimized for each type of activity during the model training phase.

Where a classifier indicates cardiac pain, a notification may be received via a wearable device and/or mobile devices associate with the user such that the user is notified to seek medical attention as early as possible. An augmented system, wearable device, and/or mobile device may transmit received ECG recording data to a general practice (GP), emergency care, and/or other medical professional.

The method may end at block 418.

These examples are merely illustrative and transaction cards may be reprogrammed according to any data described herein.

It is further noted that the systems and methods described herein may be tangibly embodied in one of more physical media, such as, but not limited to, a compact disc (CD), a digital versatile disc (DVD), a floppy disk, a hard drive, read only memory (ROM), random access memory (RAM), as well as other physical media capable of storing software, or combinations thereof. Moreover, the figures illustrate various components (e.g., servers, computers, processors, etc.) separately. The functions described as being performed at various components may be performed at other components, and the various components bay be combined or separated. Other modifications also may be made.

The present disclosure is not to be limited in terms of the particular embodiments described in this application, which are intended as illustrations of various aspects. Many modifications and variations can be made without departing from its spirit and scope, as may be apparent. Functionally equivalent methods and apparatuses within the scope of the disclosure, in addition to those enumerated herein, may be apparent from the foregoing representative descriptions. Such modifications and variations are intended to fall within the scope of the appended representative claims. The present disclosure is to be limited only by the terms of the appended representative claims, along with the full scope of equivalents to which such representative claims are entitled. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It may be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It may be further understood by those within the art that if a specific number of an introduced claim recitation is intended, such an intent may be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It may be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" may be understood to include the possibilities of "A" or "B" or "A and B."

The foregoing description, along with its associated embodiments, has been presented for purposes of illustration only. It is not exhaustive and does not limit the invention to the precise form disclosed. Those skilled in the art may appreciate from the foregoing description that modifications and variations are possible in light of the above teachings or may be acquired from practicing the disclosed embodiments. For example, the steps described need not be performed in the same sequence discussed or with the same degree of separation. Likewise various steps may be omitted, repeated, or combined, as necessary, to achieve the same or similar objectives. Accordingly, the invention is not limited to the above-described embodiments, but instead is defined by the appended claims in light of their full scope of equivalents.

In the preceding specification, various preferred embodiments have been described with references to the accompanying drawings. It may, however, be evident that various modifications and changes may be made thereto, and additional embodiments may be implemented, without departing from the broader scope of the invention as set forth in the claims that follow. The specification and drawings are accordingly to be regarded as an illustrative rather than restrictive sense.

The invention claimed is:

1. A device comprising:
an input/output interface that:
receives data indicative of chest pain;
transmits a notification to begin electrocardiogram (ECG) measurements; and
a processor that:
generates a set of instructions for a user, wherein the set of instructions includes instructions with varying levels of difficulty of exercise;
receives a set of measurements from a wearable device housing an ECG sensor comprising a heartrate measurement and at least one ECG feature, wherein the set of measurements are received as the user is following the generated set of instructions, and wherein the ECG features comprise at least one of: Karhunen-Loeve transform (KLT) components of an ST segment of the ECG measurement or a PQ segment of the ECG measurement, a time interval from R peak to P off-set and P peak, a time interval from R peak to S, and a time interval from S to J point;
classifies an ischemic change as cardiac or non-cardiac to:
determine a first feature based on a variation in activity level of the user and a variation in the detected heartrate measurement, wherein the first feature is a first weighted value when (a) there is no variation in the activity level and no variation in the heartrate measurement, (b) there is a decrease in the activity level and no variation in the heartrate measurement, (c) there is an increase in the activity level and an increase in the heartrate measurement, (d) there is an increase in the activity level and a decrease in the heartrate measurement, or (e) there is a decrease in the activity level and a decrease in the heartrate measurement, and wherein the first feature is a second weighted value when there is a decrease in the activity level and an increase in the heartrate measurement, and wherein the first weighted value <the second weighted value;
determine a second feature based on a variation in the detected ECG features and the first feature, wherein the first and second features are quantitative features; and
subject the first feature and the second feature to a cardiac pain classifier to determine a cardiac classification, wherein both the first feature and second feature are determined while bypassing usage of one or more of the following surrogate signals: a blood pressure surrogate signal, a temperature surrogate signal, and a respiratory rate surrogate signal; and
transmit the cardiac classification via the input/output interface.

2. The device of claim 1, wherein the classifying step comprises subjecting the ECG feature along with the first feature and the second feature to the cardiac pain classifier.

3. The device of claim 1, wherein the set of instructions for the user with varying levels of difficulty of exercise are generated based on a detected initial ischemic change measured using the wearable device while the user is non-ambulatory.

4. The device of claim 1, wherein the activity level comprises at least one of: a mean value of activity level measurements, a moving average of activity level measurements, an active time associated with activity level measurements, a moving average of variation in activity level measurements, a moving average of an active time associated with activity level measurements, a distance, a number of steps, and an elevation.

5. The device of claim 1, wherein the activity level comprises at least one of: a distance measurement, a step count measurement, and a speed measurement.

6. The device of claim 1, wherein the cardiac pain classifier is a support vector machine (SVM) classifier.

7. The device of claim 1, wherein the heartrate measurement comprises at least one of: a variability of heartrate within a predefined interval and a moving average of variation in heartrate computed during the predefined interval.

8. The device of claim 1, wherein the second feature is a third weighted value when there is a variation in the at least one ECG feature and the first feature is the first weighted value, and wherein the second feature is a fourth weighted value when there is a variation in the at least one ECG feature and the first feature is the second weighted value, and wherein the third weighted value <the fourth weighted value.

9. The device of claim 1, wherein classifying the ischemic change occurs continuously during an amount of time, wherein the amount of time comprises a predefined initial value that dynamically changes based on feedback from the classifying.

10. A method comprising:
receiving, via an input/output interface, data indicative of chest pain;
generating, in response to the received data indicative of chest pain, a notification to begin electrocardiogram (ECG) measurements;
generating, via a processor, a set of instructions for a user, wherein the set of instructions includes instructions with varying levels of difficulty of exercise;
receiving a set of measurements from a wearable device housing an ECG sensor comprising a heartrate measurement and at least one ECG feature, wherein the set of measurements are received as the user is following the generated set of instructions, and wherein the ECG features comprise at least one of: Karhunen-Loeve transform (KLT) components of an ST segment of the ECG measurement or a PQ segment of the ECG measurement, a time interval from R peak to P off-set and P peak, a time interval from R peak to S, and a time interval from S to J point;
classifying an ischemic change as cardiac or non-cardiac by:
determining a first feature based on a variation in activity level of the user and a variation in the detected heartrate measurement, wherein the first feature is a first weighted value when (a) there is no variation in the activity level and no variation in the heartrate measurement, (b) there is a decrease in the activity level and no variation in the heartrate measurement, (c) there is an increase in the activity level and an increase in the heartrate measurement, (d) there is an increase in the activity level and a decrease in the heartrate measurement, or (e) there is a decrease in the activity level and a decrease in the heartrate measurement, and wherein the first feature is a second weighted value when there is a decrease in the activity level and an increase in the heartrate measurement, and wherein the first weighted value <the second weighted value;

determining a second feature based on a variation in the detected ECG features and the first feature, wherein the first and second features are quantitative features; and subjecting at least the first feature and the second feature to a cardiac pain classifier to determine a cardiac classification, wherein both the first feature and second feature are determined while bypassing usage of one or more of the following surrogate signals: a blood pressure surrogate signal, a temperature surrogate signal, and a respiratory rate surrogate signal; and transmitting the cardiac classification via the input/output interface.

11. The method of claim 10, wherein the classifying step comprises subjecting the ECG feature along with the first feature and the second feature to the cardiac pain classifier.

12. The method of claim 10, wherein the set of instructions for the user with varying levels of difficulty of exercise are generated based on a detected initial ischemic change measured using the wearable device while the user is non-ambulatory.

13. The method of claim 10, wherein the activity level comprises at least one of: a mean value of activity level measurements, a moving average of activity level measurements, an active time associated with activity level measurements, a moving average of variation in activity level measurements, a moving average of an active time associated with activity level measurements, a distance a number of steps, and an elevation.

14. The method of claim 10, wherein the activity level comprises at least one of: a distance measurement, a step count measurement, and a speed measurement.

15. The method of claim 10, wherein the cardiac pain classifier is a support vector machine (SVM) classifier.

16. The method of claim 10, wherein the heartrate measurement comprises at least one of: a variability of heartrate within a predefined interval and a moving average of variation in heartrate computed during the predefined interval.

17. The method of claim 10, wherein the second feature is a third weighted value when there is a variation in the at least one ECG feature and the first feature is the first weighted value, and wherein the second feature is a fourth weighted value when there is a variation in the at least one ECG feature and the first feature is the second weighted value, and wherein the third weighted value <the fourth weighted value.

18. The method of claim 10, wherein classifying the ischemic change occurs continuously during an amount of time, wherein the amount of time comprises a predefined initial value that dynamically changes based on feedback from the classifying.

* * * * *